(12) United States Patent
Eghtesady

(10) Patent No.: US 8,529,514 B2
(45) Date of Patent: Sep. 10, 2013

(54) CANNULA WITH REMOVABLE SLEEVE

(75) Inventor: Pirooz Eghtesady, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1145 days.

(21) Appl. No.: 11/429,395

(22) Filed: May 5, 2006

(65) Prior Publication Data

US 2007/0260218 A1 Nov. 8, 2007

(51) Int. Cl.
*A61M 5/178* (2006.01)

(52) U.S. Cl.
USPC ................................ 604/164.01; 604/44

(58) Field of Classification Search
USPC .................. 604/164.01–164, 510–523, 44
See application file for complete search history.

(56) References Cited

U.S. PATENT DOCUMENTS

| | | | | |
|---|---|---|---|---|
| 2,393,002 A * | 1/1946 | Smith | | 604/43 |
| 4,099,528 A * | 7/1978 | Sorenson et al. | | 604/44 |
| 4,333,455 A * | 6/1982 | Bodicky | | 604/158 |
| 5,348,545 A | 9/1994 | Shani et al. | | |
| 5,562,606 A | 10/1996 | Huybregts | | |
| 6,042,576 A * | 3/2000 | DeVries | | 604/523 |
| 6,440,120 B1 | 8/2002 | Maahs | | |
| 6,533,770 B1 | 3/2003 | Lepulu et al. | | |
| 6,626,872 B1 | 9/2003 | Navia et al. | | |
| 6,673,042 B1 | 1/2004 | Samson et al. | | |
| 2006/0030864 A1 * | 2/2006 | Kennedy et al. | | 606/108 |
| 2008/0097193 A1 * | 4/2008 | Karmarkar | | 600/423 |

FOREIGN PATENT DOCUMENTS

| | | |
|---|---|---|
| WO | WO9739789 | 10/1997 |
| WO | WO2006/014966 | 2/2006 |
| WO | PCT/US07/10683 | 10/2008 |
| WO | PCT/US07/10683 | 11/2008 |

OTHER PUBLICATIONS

Seldinger Technique, interactive website, http://www.frca.co.uk/article.aspx?articleid=100029, date unknown but prior to May 5, 2006.

* cited by examiner

*Primary Examiner* — Kevin C Sirmons
*Assistant Examiner* — Phillip Gray
(74) *Attorney, Agent, or Firm* — Taft Stettinius & Hollister LLP

(57) ABSTRACT

A venous cannula is disclosed having an insertion hole near the distal end and a leading end hole at the distal end. The cannula further includes a removable sleeve that is fitted within the insertion hole and preferably extends at least from the insertion hole to the leading end hole. In a preferred embodiment, the cannula also includes an introducer that fits within the removable sleeve and extends at least the length of the removable sleeve. The removable sleeve and introducer are designed to facilitate use of the Seldinger technique with the venous cannula. Additionally, a method for use of the Seldinger technique with the cannula is disclosed.

19 Claims, 9 Drawing Sheets

CANNULA WITH REMOVABLE SLEEVE

FIELD OF THE INVENTION

The present invention is directed to the field of intraluminal devices and, more specifically, to methods and devices facilitating such methods for the use of the Seldinger technique with a cannula.

BACKGROUND

Cannulae are used in part during cardiopulmonary bypass to maintain circulation of blood through a patient's body. A cannula is inserted into the patient's venous system to drain blood, and the blood is then returned with the use of a cannula in combination with a heart-lung machine to the arterial system of the patient.

Cannulae are made in various sizes to match the patient size. These cannulae generally come in three forms: straight, straight with additional end holes (used primarily for extracorporeal membrane oxygenation ("ECMO")), and rightangled. A right angle cannula is used primarily as a specific type of venous cannula to drain blood from the right side (or venous end) of the heart—that is, it allows cannulation of the vena cava.

Introduction of a venous cannula into a patient requires special surgical skill. In the usual situation, at least two surgeons/surgical assistants are needed to introduce the venous cannula into the patient due to the difficulty of inserting the cannula while making the necessary cut, placing the required sutures, and maintaining the opening. Moreover, the complexity of the introduction of the cannula is related to the size and the location of the vessel (i.e., the ease with which the vessel can be accessed, managed, and manipulated). In a fetal patient or premature newborn, the small vessels and small surgical and visual fields limit the feasibility of surgically using these cannulae. Similarly, in minimally invasive and robotic surgery, use of the traditional cannulae is made more challenging by the intrinsic distance from the surgical field as well as the limited access to the targeted area and indirect interaction with the vessel. Additionally, with all cannulations, the introduction of current cannulae into vessels oftentimes results in limited yet significant blood loss. To overcome these problems, and others, a new cannula is disclosed.

SUMMARY

The cannula of the present invention has a leading end hole at its leading end to drain the inferior vena cava and an insertion hole distal from the leading end. The cannula further includes a removable sleeve that is fitted into the insertion hole and out through the leading end hole at the leading end. In some embodiments, a portion of the removable sleeve extends out of the insertion hole and/or leading end hole of the cannula. In an exemplary embodiment, an upper portion of the removable sleeve fits snugly around the insertion hole.

In an exemplary embodiment, the venous cannula has a substantially right angle bend near the leading end of the cannula. In such an embodiment, the insertion hole is generally located at the heel of the right angle bend, generally along the axis of the leading end hole, to allow for introduction of the removable sleeve into the cannula generally along the axis of the insertion and leading end holes.

In another exemplary embodiment, the venous cannula has an acute bend or an obtuse bend near the leading end of the cannula. In yet other exemplary embodiments, the cannula is substantially straight (i.e., no manufactured bend near the leading end), and the cannula includes an angled insertion hole distal from the leading end (where the axis of the insertion hole is substantially angled with respect to the axis of the leading end hole), which in turn requires the removable sleeve to be flexible and/or angled to correspond to the angled drainage and insertion holes.

In yet another exemplary embodiment, the cannula includes both the removable sleeve and an introducer. While an exemplary embodiment of the present invention may include both the removable sleeve and the introducer, the function of the introducer can be built into the removable sleeve. Accordingly, the introducer is not required in an exemplary embodiment of the present invention.

The introducer fits within the removable sleeve and extends at least the length of the removable sleeve. The introducer is generally designed to further assist in facilitating the use of the Seldinger technique with the cannula. The introducer may be narrower at its distal end in order to more easily be introduced into the vessel. Preferably, the introducer would be tapered at its leading end; its leading end would be the narrowest and then it would widen for a desired length moving from the leading end distally therefrom. The guidewire—for use of the Seldinger technique—would be slidably disposed within the shaft of the introducer and/or the removable sleeve.

THEREFORE, it is a first aspect of the present invention to provide a cannula that includes: an elongated tubular body having a proximal end and leading end, the body having a first opening at the leading end and a second opening at the proximal end, and the body having a third opening distal from the leading end; a removable sleeve that extends at least from the third body opening to the first body opening, and the sleeve having an open proximal end and open leading end; the removable sleeve is substantially straight in order to be able to guide the removable sleeve along a guidewire; the first and third body openings being no more than 6.35 cm apart.

It is a second aspect of the present invention to provide a method of introducing a cannula into a vessel, including the steps of: (a) providing a cannula that includes: an elongated tubular body having a proximal end and leading end, the body having a first opening at the leading end and a second opening at the proximal end, and the body having a third opening distal from the leading end; a removable sleeve that extends at least from the third body opening to the first body opening, and the sleeve having an open proximal end and open leading end; the removable sleeve is substantially straight in order to be able to guide the removable sleeve along a guidewire; the first and third body openings being no more than 6.35 cm apart; (b) providing an opening into a vessel and using a suture to maintain the opening; (c) inserting a needle into the vessel at the opening, the needle having a shaft that extends the entirety of the needle; the needle being open at both the top of the shaft and bottom of the shaft; (d) threading one end of a guidewire through the needle and into the vessel; (e) removing the needle over the guidewire; (f) threading the other end of guidewire through the removable sleeve and leading end of the cannula body from the opening at the leading end of the sleeve through the opening at the proximal end of the sleeve; (g) moving the leading end of the cannula body and removable sleeve down the length of the guidewire to a position abutting the opening of the vessel; (h) inserting a portion of the leading end of the cannula body and at least a portion of the leading end of the removable sleeve into the vessel; and (i) removing the removable sleeve from the leading end of the cannula body.

DETAILED DESCRIPTION

It should be understood that the following detailed description of exemplary embodiments of the invention are exemplary in nature and are not intended to constitute limitations upon the invention. It is also to be understood that variations of the exemplary embodiments contemplated by one of ordinary skill in the art shall concurrently fall within the scope and spirit of the invention. Although certain aspects of the exemplary embodiments are shown in more detail, some features within the purview of one skilled in the art may have been omitted for the sake of clarity and brevity.

Figure 1:
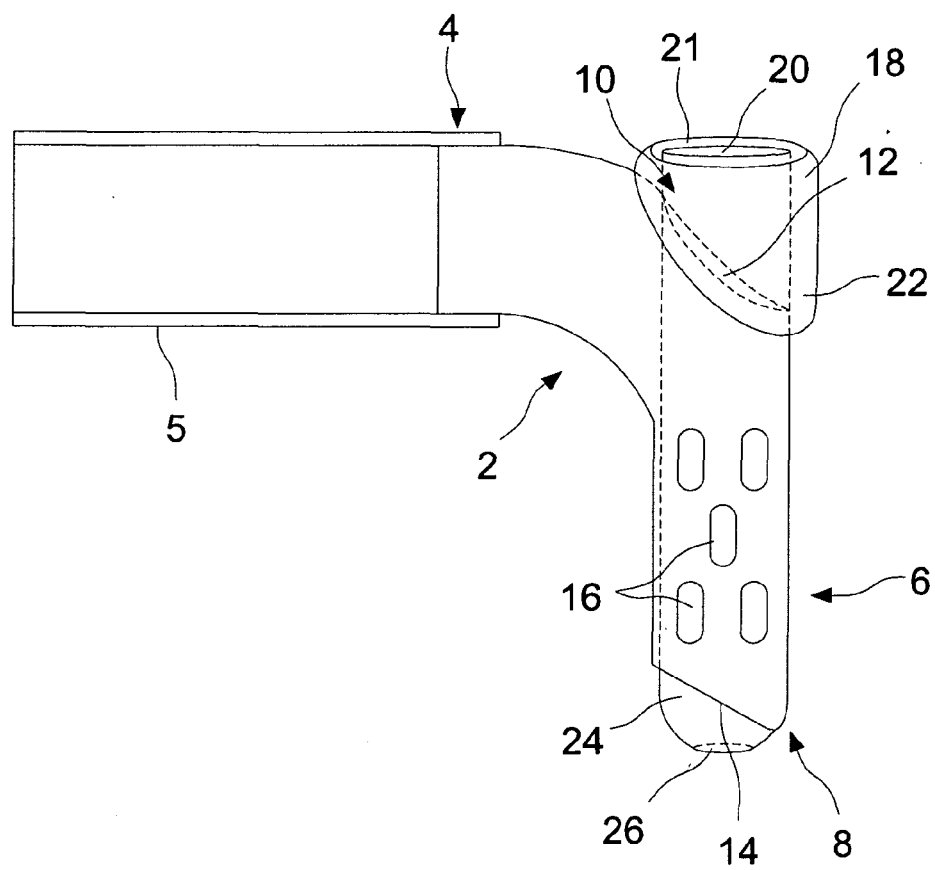
FIG. 1 is a side, partial cross-sectional view of an exemplary embodiment of the present invention.

Referring to FIG. 1, a cannula according to an exemplary embodiment of the present invention includes a right-angled cannula head 2 having a proximal segment 4 mounted to and in fluid communication with the cannula tubing 5 and a distal segment 6 angled at substantially a ninety degree angle with the proximal segment 4. The distal segment 6 includes an open leading end 8. The cannula may include one or more interior lumens extending therethrough.

In the exemplary embodiment of FIG. 1, the cannula head 2 is bent at a heel 10 to approximately form a substantially right angle. In other embodiments, the cannula head 2 may be bent at the heel 10 to form an acute angle or an obtuse angle. In yet other embodiments (such as described below), the cannula or the cannula head may be substantially straight (i.e., not substantially bent at the heel 10).

Referring again to FIG. 1, the cannula head 2 has an insertion hole 12 near the heel 10 and a leading end hole 14 at the leading end 8. The axis of the insertion hole 12 is substantially along the axis of the leading end hole 14. In exemplary embodiments, the distance between the insertion hole 12 and the leading end hole 14 varies from approximately 0.5 cm to 4.5 cm depending on the size of the cannula. At most, the distance from the insertion hole 12 to the leading end hole 14 is 6.35 cm. In the exemplary embodiment of FIG. 1, the cannula head 2 includes an additional plurality of side holes 16 uniformly distributed about the circumference of the distal segment 6 of the cannula head 2. Such additional holes 16, located near the leading end 8 of the cannula head 2, assist the leading end hole 14 to drain the inferior vena cava in the exemplary embodiment. It is to be understood that the use of the cannula of the present invention is not limited to the inferior vena cava and may also be used in the superior vena cava and other vessels.

As disclosed in FIG. 1, a removable, tubular sleeve 18 fits into the insertion hole 12 and extends from the insertion hole 12 at the heel through the leading end hole 14, substantially along the axis of the insertion and leading end holes 12, 14. The removable sleeve 18 has a sleeve interior lumen 20 that is open at a sleeve proximal end 22 and a sleeve leading end 24. The opening at the sleeve lending end is identified in FIG. 1 as a sleeve leading end hole 26.

In the exemplary embodiment, a portion of the removable sleeve 18 and sleeve interior lumen 20 extends out of both of the insertion hole 12 and the leading end hole 14. Further, the portion of the removable sleeve 18 extending out through the insertion hole 12 includes an annular shoulder portion 21 that is shaped to abut and fit snugly about the outer surface of the cannula head 2 at the heel 10, encircling the insertion hole 12. The portion of the removable sleeve 18 extending out beyond the leading end hole 14 is tapered such that the diameter of the removable sleeve 18 at the sleeve leading end hole 26 is smaller than the diameter of the removable sleeve 18 at the leading end hole 14 and gradually increases to the size of the opening at the leading end hole 14. The tapered design of the sleeve leading end 24 facilitates delivery of the cannula head 2 into a vessel with minimal trauma.

The removable sleeve 18 of the exemplary embodiment is made of a semi-rigid, plastic material. In other exemplary embodiments, the removable sleeve is composed of rigid materials such as steel and/or flexible materials such as a rubber.

Figure 2:
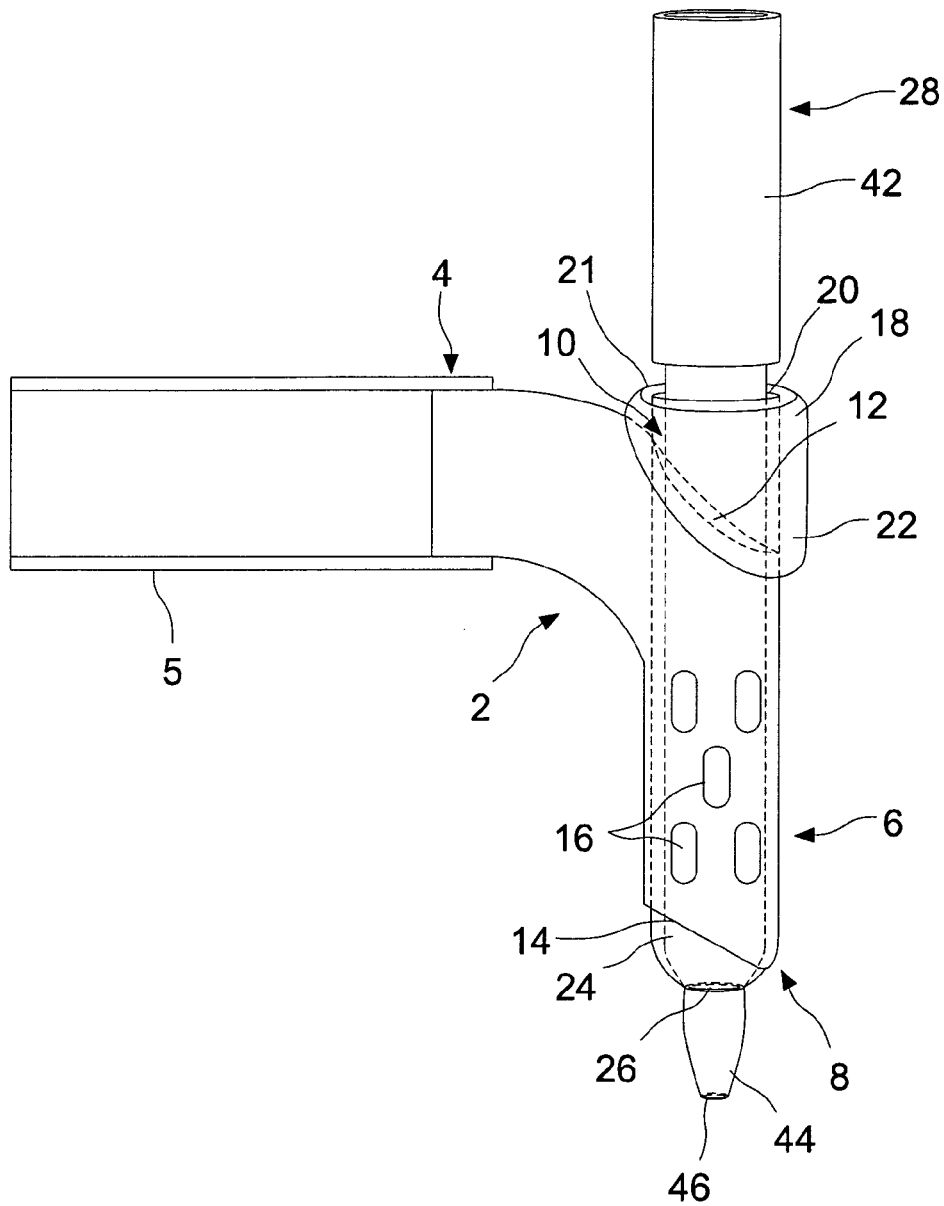
FIG. 2 is a side, partial cross-sectional view of the exemplary embodiment of FIG. 1 with an introducer of the present invention included.

Referring to FIG. 2, the cannula 2 is shown with a tubular introducer 28 inserted through the interior lumen 20 of the removable sleeve 18. While an exemplary embodiment of the present invention may include both the removable sleeve 18 and the introducer 28, the function of the introducer 28 (discussed below) can be built into the removable sleeve 18. Accordingly, an introducer 28 is not required to be included in all exemplary embodiments of the cannula of the present invention.

The introducer has an introducer proximal end 42, an introducer leading end 44, and an introducer leading end hole 46. In this exemplary embodiment, the introducer 28 extends at least the length from the insertion hole 12 to the leading end hole 14 and extends out of both of the removable sleeve's open proximal end 22 and leading end 24.

The introducer is generally designed to assist in facilitating the use of the Seldinger technique with the cannula. In the exemplary embodiment of FIG. 2, the introducer 28 is thicker at the introducer proximal end 42. This thicker portion of the introducer 28 in part acts as a stopper for the introducer when it is inserted into the opening of the sleeve proximal end 22 of the removable sleeve 18. As such, the thickness of the introducer proximal end 42 stops the introducer leading end 44 from extending further out through the sleeve leading end hole 26. The thicker portion of the introducer 28 also can be used to provide a better grip on the introducer 28 and allow for the introducer to be more easily removed from the cannula head 2. As noted, in an exemplary embodiment, the introducer 28 also extends out of the sleeve leading end 24. In an exemplary embodiment, the introducer 28 is narrower at the leading end 44 in order to be more easily introduced into the vessel or cavity; and, more specifically, the introducer 28 is tapered at the introducer leading end 44 such that its diameter widens with the distance from the introducer leading end hole 46. The diameter of the introducer 28 gradually increases with the distance from the introducer leading end hole 46 to the sleeve leading end hole 26, and the diameter of the removable sleeve 18 gradually increases with the distance from the sleeve leading end hole 26 to the leading end hole 14 of the cannula head 2. In an exemplary embodiment of the invention, the introducer leading end hole 46 may be significantly smaller in diameter than even sleeve leading end hole 26 such that the opening at introducer leading end hole 46 is only slightly larger in diameter than a guidewire 38 (see FIGS. 6-8) over which the cannula head 2 would be introduced. The tapered end of the sleeve leading 24 and the introducer leading end 44 are designed to assist the surgeon in locating and inserting the cannula within a small opening created in a vessel. When the introducer 28 (if present in an exemplary embodiment) and the removable sleeve 18 are removed from the cannula head 2, the vessel can be drained through the larger cannula leading end hole 8 as well as the additional holes 16. In an exemplary embodiment, the openings of the sleeve leading end and the introducer leading end 26, 46 are smaller in diameter than the opening of the cannula leading end hole 8. In an exemplary embodiment, a smaller leading end (either the sleeve 18 or the sleeve in conjunction with the introducer 28) is used for introduction of the cannula. The smaller leading end is then removed so that the larger leading end hole 8 (as well as the additional holes 16 if present) of the cannula head 2 can be used for drainage.

Figure 3:
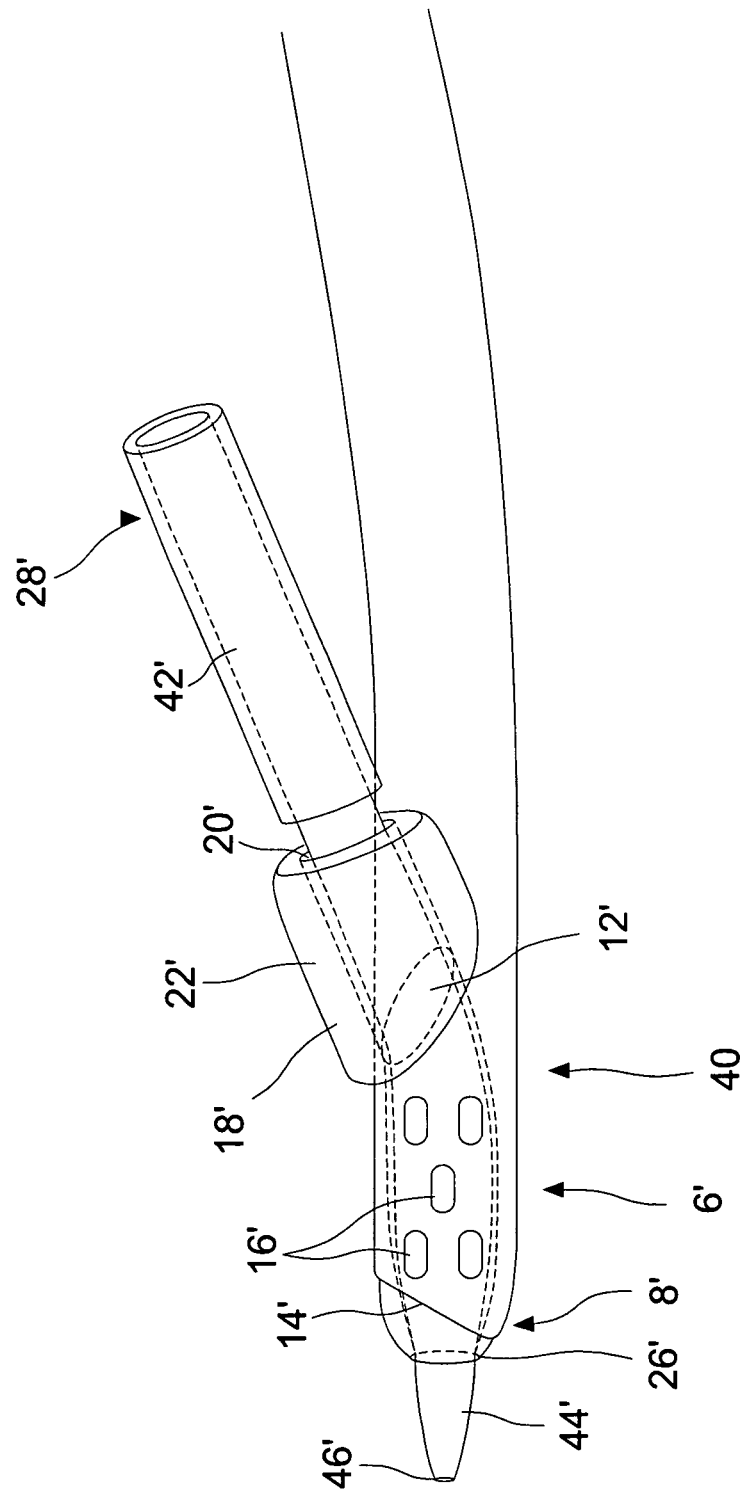
FIG. 3 is a side, partial cross-sectional view of another exemplary embodiment of the present invention.

Referring to FIG. 3, a straight cannula 40 with the removable sleeve 18' and the introducer 28', yet another exemplary embodiment, is disclosed. The straight cannula 40 has no manufactured bend. The straight cannula 40 has at least one leading end hole 14' at the leading end 8' and an insertion hole 12' distal from the leading end and extending through the side wall of the cannula 40 to allow for introduction of the flexible or angled removable sleeve 18' and introducer 28' into the straight cannula 40. In this embodiment, the cannula 40 also includes a plurality of additional holes 16' uniformly distributed about the circumference of the cannula 40 between the leading end 44 and the insertion hole 12'. Such additional removal holes 16' are located near the leading end 8' of the straight cannula 40 and assist the leading end hole 14' to drain the inferior vena cava. As noted above, use of the cannula of the present invention is not to be limited to the inferior or even the superior vena cava; an exemplary embodiment of the present invention may be used in other vessels in the body.

In some embodiments, the insertion hole 12' of the straight cannula 40 may be angled to better facilitate the introduction of the removable sleeve 18' and/or the introducer 28'. In still other embodiments, the insertion hole 12' may be larger to better facilitate the introduction of the removable sleeve 18' and/or the introducer 28'. In yet another exemplary embodiment, the insertion hole 12 may be elongated to facilitate the introduction of the removable sleeve 18' and/or the introducer 28'.

In some embodiments, a portion of the removable sleeve 18' and sleeve interior lumen 20' may extend out of the one or both of the leading end hole 8' and the insertion hole 12'. In some embodiments, a radial shoulder portion 21' of the removable sleeve 18' is shaped to abut the cannula/cannula-head about the insertion hole 12' and fit snugly around the insertion hole 12'. The removable sleeve 18' may be made of a rigid, semi-rigid, or flexible material.

Referring to FIGS. 4-8, an exemplary method of the present invention is shown. The method discloses the process of insertion of the cannula head 2 into the vena cava with the assistance of the removable sleeve 18 and introducer 28. As noted previously, an introducer 28 is not required to be included in all exemplary embodiments of the cannula of the present invention. Similarly, in some exemplary methods of the present invention, the removable sleeve 18 may be designed to perform the desired function of the introducer 28, and in such cases, the introducer 28 would not be required in order to perform an exemplary method.

Figure 4:
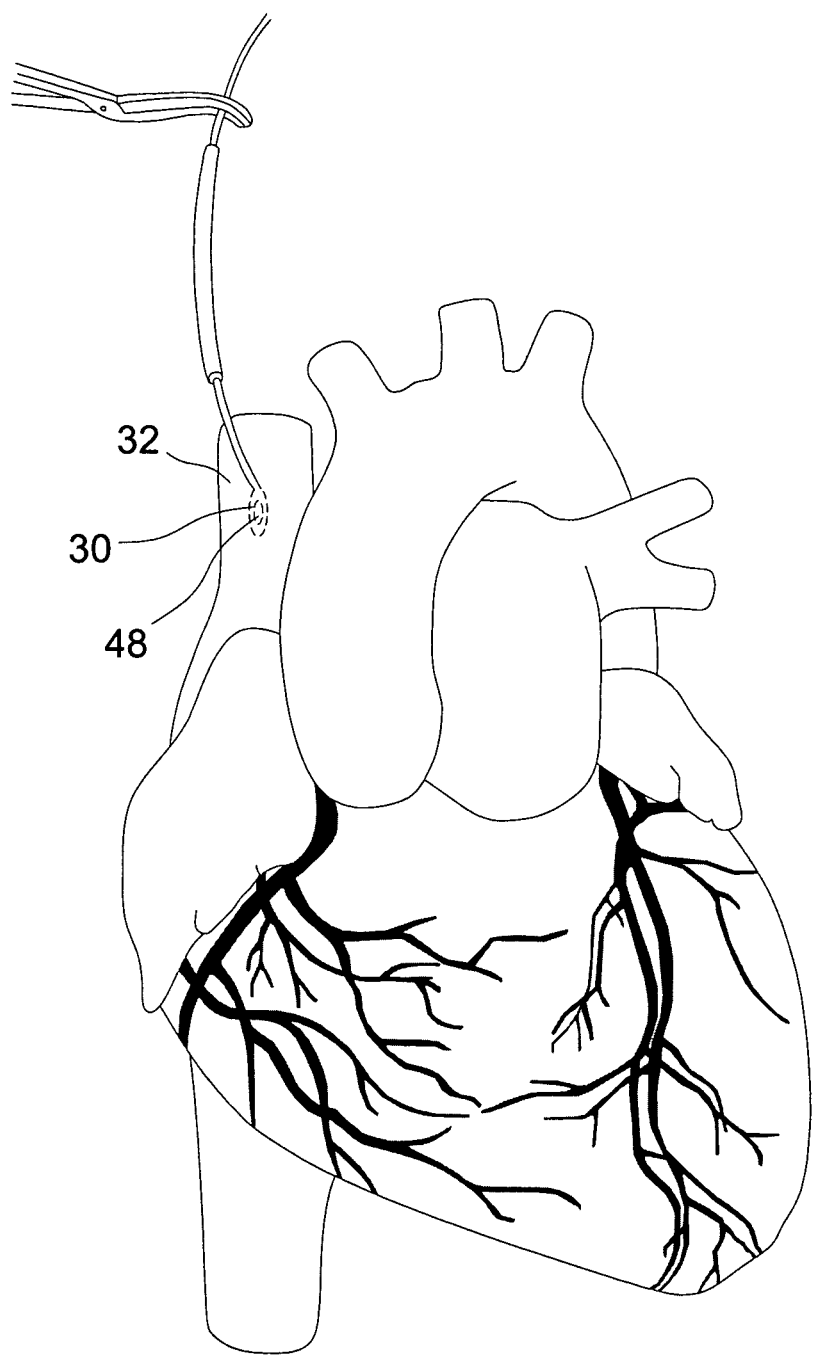
FIG. 4 is a profile view of a heart, illustrating an exemplary method step(s) according to the present invention.

Referring specifically to FIG. 4, after a small cut is made on the vessel 32, a suture 30 is placed on the vessel 32 to maintain an opening 48 to the inside of the vessel 32. In a preferred embodiment, the suture 30 is a purse-string suture.

Figure 5:
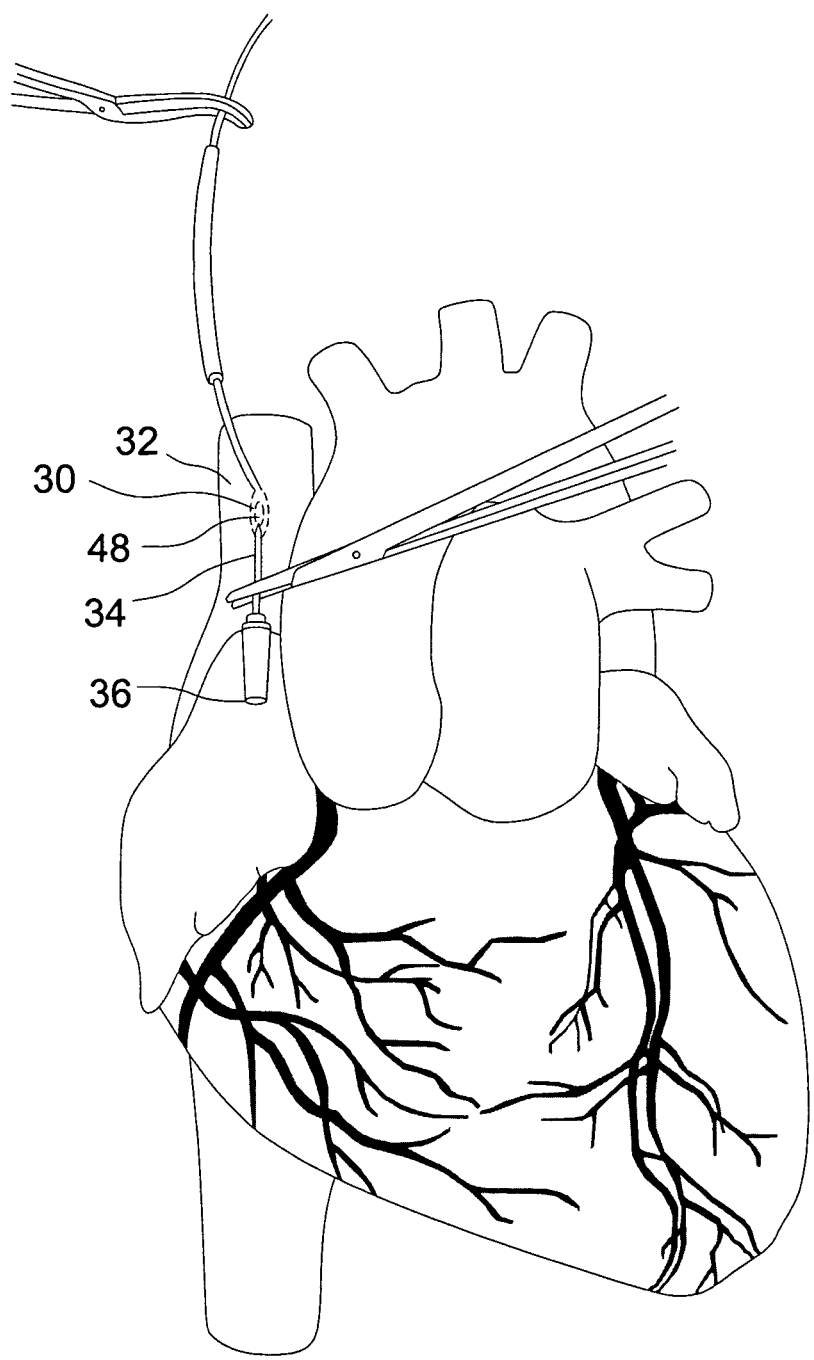
FIG. 5 is a profile view of the heart of FIG. 4, illustrating another exemplary method step(s) according to the present invention.

Referring to FIG. 5, a needle 34 is inserted into the vessel 32 within the opening 48 maintained by the suture 30. The needle 34 has a needle interior lumen 36 that extends the full length of the needle and is open at both ends of the needle 34.

Figure 6:
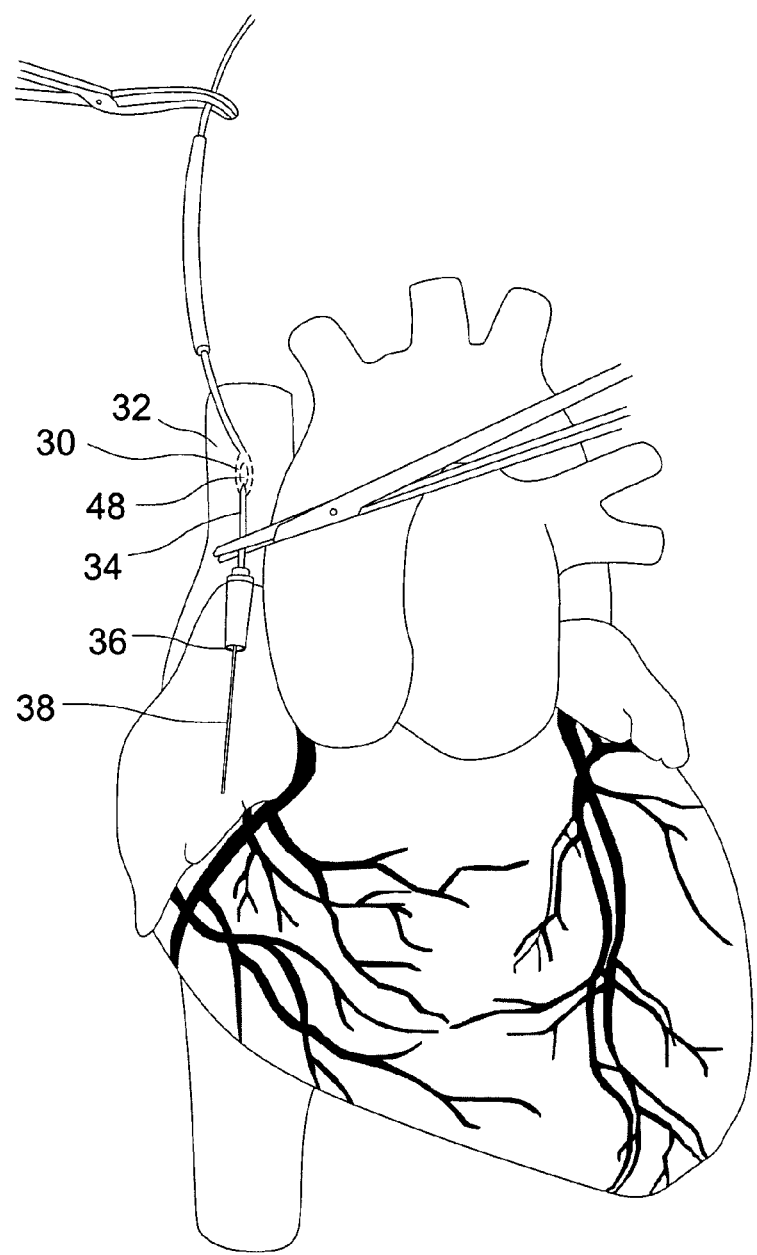
FIG. 6 is a profile view of the heart of FIG. 4, illustrating another exemplary method step(s) according to the present invention.

Referring to FIG. 6, a guidewire 38 is passed through the needle interior lumen 36 and into the vessel 32. The needle 34 is then removed over the guidewire 38. The guidewire 38 remains in the vessel 32. At this point, in an exemplary method, the introducer 28 and/or the removable sleeve 18 may be passed over the wire 38 into the vessel 32 in order to dilate the vessel prior to introduction of the cannula head 2 and then removed.

Figure 7:
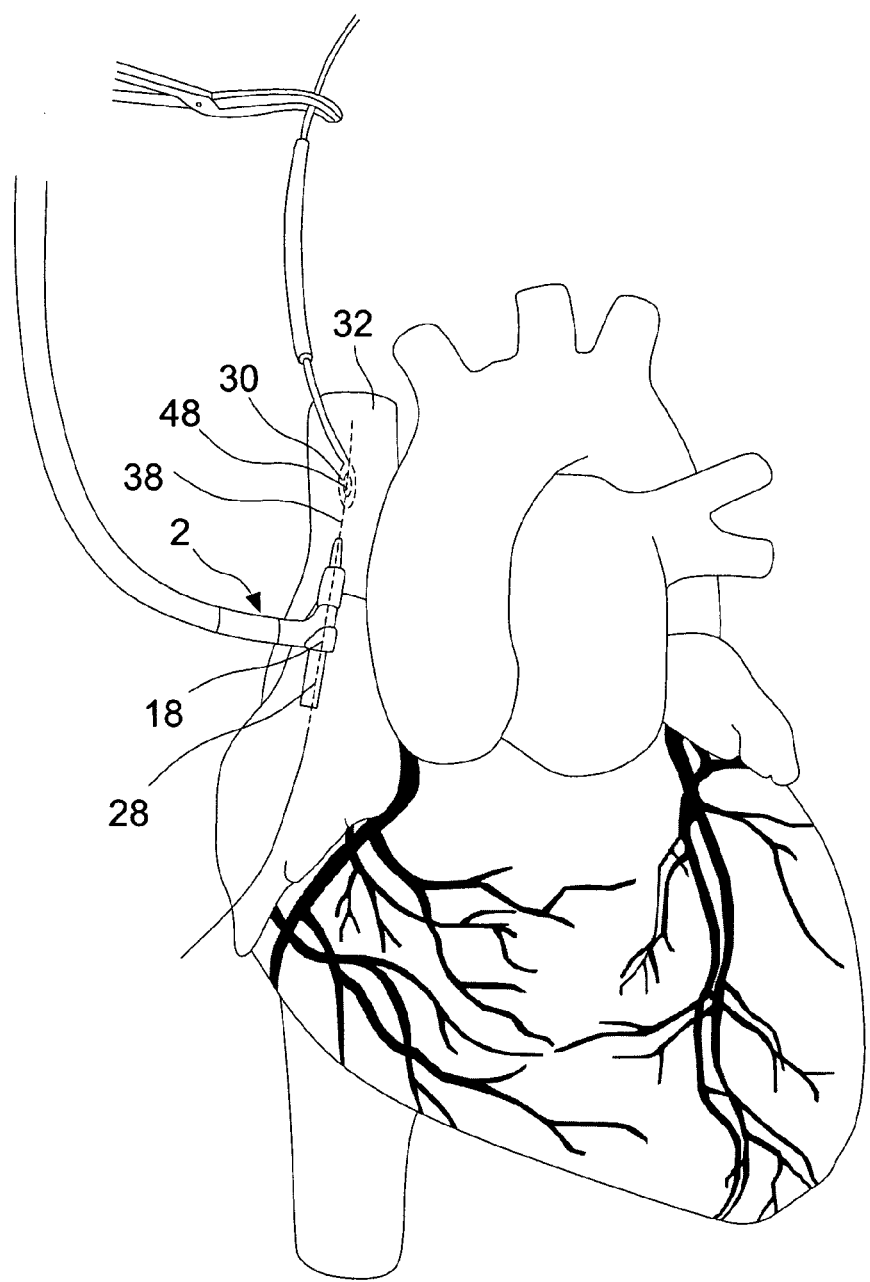
FIG. 7 is a profile view of the exemplary embodiment of FIG. 2 in use in the heart of FIG. 4, illustrating another exemplary method step(s) according to the present invention.
Figure 8:
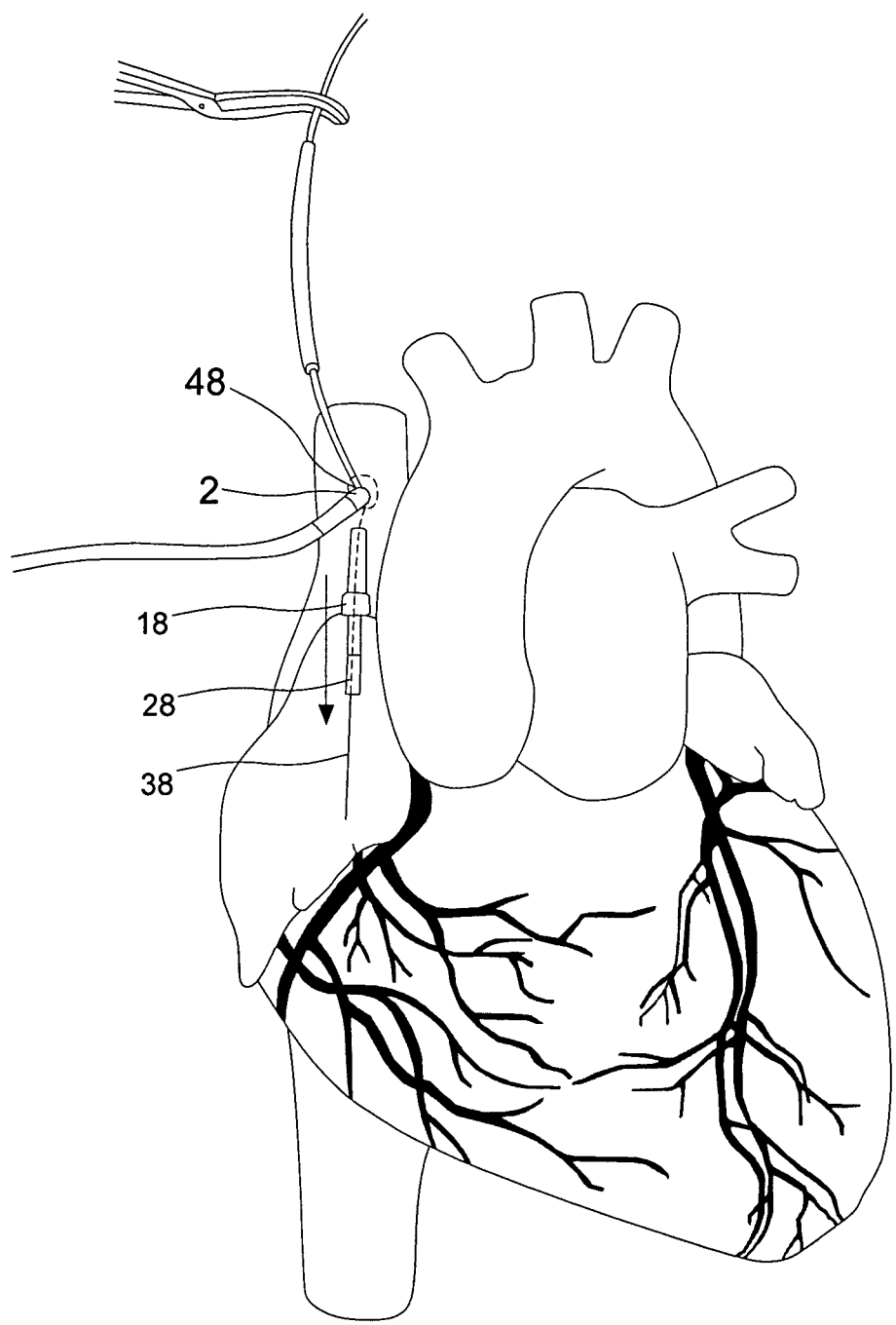
FIG. 8 is a profile view of the exemplary embodiment of FIG. 2 in use in the heart of FIG. 4, illustrating another exemplary method step(s) according to the present invention.

Referring to FIG. 7-8, in an exemplary method, one end of the guidewire 38 (opposite the end positioned within the vessel 32) is inserted into the introducer leading end hole 46 (and/or the sleeve leading end hole 26), through the sleeve interior lumen 20, and out of the opening at the introducer proximal end 42 (and/or the sleeve proximal end 22). As such, the guidewire 38 is threaded substantially through the distal segment 6 of the cannula head 2. The cannula head 2, removable sleeve 18, and introducer 28 are moved over the guidewire 38 to a position abutting the opening 48. The cannula leading end 8, sleeve leading end 26, and introducer leading end 46 are then inserted through the opening 48 and into the vessel 32. With the cannula leading end 8 positioned in the vessel 32, the removable sleeve 18 and introducer 28 are detached from the cannula head 2 and removed from the vessel 32. The removable sleeve 18 and introducer 28 are then moved along the guidewire 38 away from the vessel 32 and removed from the guidewire 38. In a preferred method, the entire distal end segment 6 (from the leading end hole 14 to beyond the heel 10) is advanced into the vessel 32. With a significant portion of the cannula head 2 positioned within the vessel 32, the opening 48 is tightened about the cannula proximal end 4 and/or the cannula tubing 5 by use of the suture. Substantially closing the opening in this manner helps prevent the cannula from falling out of the vessel. The process of introducing the cannula head 2 into the vessel 32 is completed. Thereafter, the leading end hole 14, side holes 16 and insertion hole 12 all facilitate drainage from the vessel 32.

Figure 9:
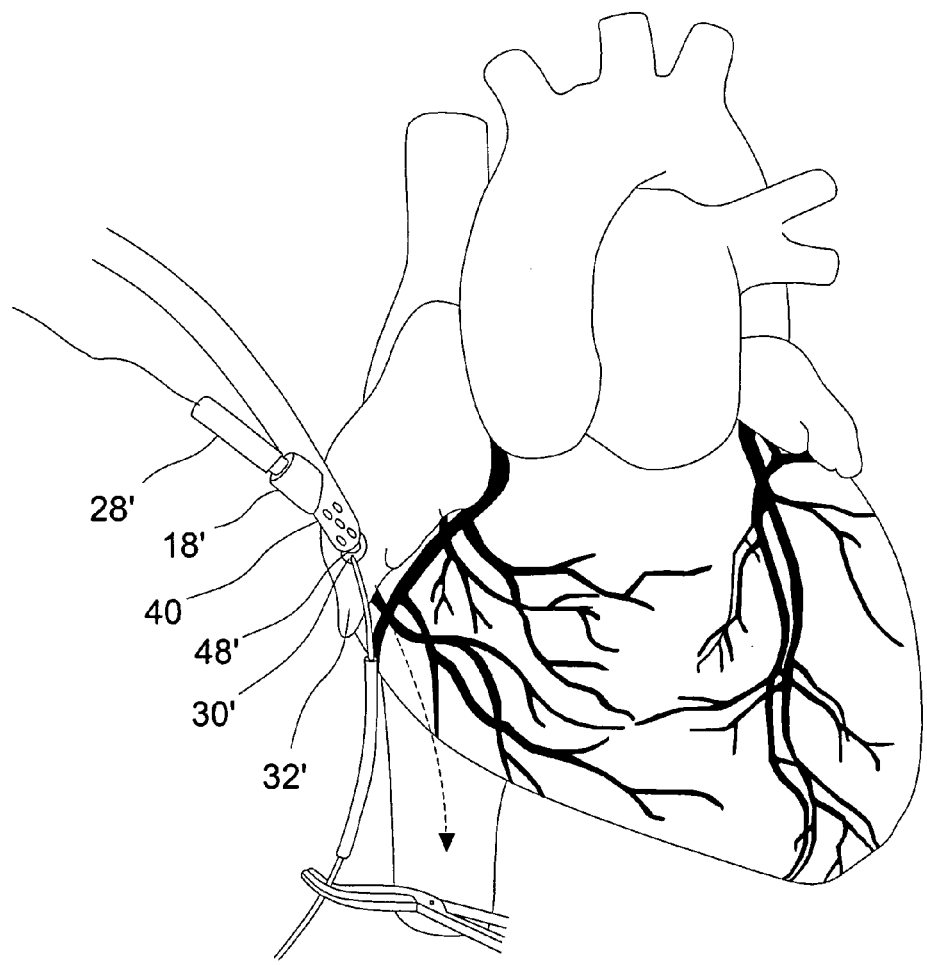
FIG. 9 is a profile view of the exemplary embodiment of FIG. 3 in use in the heart of FIG. 4, illustrating an alternate exemplary method step(s) according to the present invention.

Referring to FIG. 9, a straight angle cannula 40 of the present invention is shown introduced into a vessel 32' of the heart, prior to removal of the removable sleeve 18' and introducer 28'. In an exemplary method of the present invention, a substantially similar method is followed for introduction of the straight angle cannula 40 into the vessel 32' as was used for introduction of the right-angled cannula head 2 into the vessel 32, whereby a small cut is made on the vessel 32' and an opening into the vessel is created, the opening is maintained by a purse-string suture, a needle is placed into the opening, a guidewire is threaded through the needle into the opening, the needle is removed from the guidewire, the distal segment 6' of the straight angle cannula 40 as well as the removable sleeve 18' and introducer 28' are placed on the guidewire, the leading end 8' of the straight angle cannula 40' as well as the sleeve leading end 24' and introducer leading end 44' are then positioned within the vessel.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiments and that changes may be made without departing from the scope of the invention. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A cannula comprising:
    an elongated tubular body including
        a distal segment, the distal segment including a distal segment leading end face at a leading end of the distal segment and a distal segment proximal end, the distal segment including a first opening extending generally axially through the leading end face at the leading end of the distal segment and a third opening extending through the distal segment proximal end, and
        a proximal segment fluidicly coupled to the distal segment near the third opening, the proximal segment including a proximal segment proximal end and a second opening at a proximal segment proximal end, the proximal segment proximal end being for fluidicly coupling to a section of tubing; and
    a removable tubular sleeve extending through the third opening, within the tubular body at least from the third opening to the first opening, and through the first opening, the removable sleeve having a sleeve proximal end face including a sleeve proximal opening extending through the sleeve proximal end face and a sleeve leading end including a sleeve leading end face including a sleeve leading end hole extending through the sleeve leading end face, the removable tubular sleeve defining a sleeve interior lumen extending from the sleeve proximal opening to the sleeve leading end hole;
    wherein the removable tubular sleeve is one of substantially straight and slightly angled so as to facilitate guidance of the removable tubular sleeve along a guidewire, the removable tubular sleeve being adapted to receive the guidewire through the sleeve interior lumen; and
    wherein the first and third opening are spaced from each other by at most 6.35 centimeters.

2. The cannula of claim 1, wherein at least a portion of the sleeve leading end extends beyond the first opening when the removable sleeve is fully inserted into the tubular body via the third opening.

3. The cannula of claim 1, wherein a diameter of the sleeve leading end hole is smaller than a diameter of the first opening.

4. The cannula of claim 2, wherein the portion of the sleeve leading end that extends beyond the first opening is smaller in diameter than the first opening.

5. The cannula of claim 1, wherein a diameter of the removable sleeve at the first opening is greater than a diameter of the removable sleeve at the sleeve leading end hole.

6. The cannula of claim 1, further comprising a tubular introducer fitted through the interior lumen of the removable sleeve from the sleeve proximal opening to the sleeve leading end hole.

7. The cannula of claim 6, wherein the introducer includes an introducer proximal end nearest the sleeve proximal end face and an introducer leading end nearest the sleeve leading end face, and wherein at least a portion of the introducer leading end extends through the sleeve leading end hole when the introducer is fully inserted into the removable sleeve via the sleeve proximal opening.

8. The cannula of claim 7 wherein the introducer has a substantially tapered leading end.

9. The cannula of claim 7, wherein the portion of the introducer leading end that extends through the sleeve leading end is smaller in diameter than the sleeve leading end hole.

10. The cannula of claim 7, wherein a portion of the introducer proximal end extends out of the sleeve proximal opening.

11. The cannula of claim 10 wherein the portion of the introducer proximal end that extends out of the sleeve proximal opening is larger in diameter than the sleeve proximal opening.

12. The cannula of claim 1 wherein the tubular body is angled about a heel.

13. The cannula of claim 12, wherein the third opening is located at the heel.

14. The cannula of claim 12, wherein the proximal segment is angled away from the distal segment to approximately form a right angle.

15. The cannula of claim 12, wherein the first opening and the third opening lie substantially along a central axis of the distal segment.

16. The cannula of claim 1, wherein the third opening is provided on the tubular body of a substantially straight cannula.

17. The cannula of claim 1, wherein the distal segment includes at least one lateral opening between the first opening and third opening.

18. The cannula of claim 1, wherein the removable sleeve includes an annular shoulder near the proximal end face, the annular shoulder being shaped to abut and encircle the third opening.

19. The cannula of claim 1 wherein the first and third openings are spaced from each other at a distance no less than 0.5 cm and no more than 4.5 cm.

* * * * *